(12) United States Patent
Thorgersen et al.

(10) Patent No.: US 9,975,792 B2
(45) Date of Patent: *May 22, 2018

(54) WATER-DISSOLVABLE DEVICE FOR TREATMENT OF WASTE MATERIAL

(75) Inventors: Vincent J. Thorgersen, Hampshire, IL (US); John H. Bacon, Sugar Grove, IL (US); Eric D. Frazier, Marengo, IL (US)

(73) Assignee: UNITED LABORATORIES, INC., St. Charles, IL (US)

( * ) Notice: Subject to any disclaimer, the term of this patent is extended or adjusted under 35 U.S.C. 154(b) by 1573 days.

This patent is subject to a terminal disclaimer.

(21) Appl. No.: 13/083,241

(22) Filed: Apr. 8, 2011

(65) Prior Publication Data

US 2012/0255901 A1    Oct. 11, 2012

(51) Int. Cl.
*C02F 1/68* (2006.01)
*C12N 1/20* (2006.01)
*C02F 1/72* (2006.01)

(52) U.S. Cl.
CPC ............... *C02F 1/688* (2013.01); *C12N 1/20* (2013.01); *C02F 1/722* (2013.01)

(58) Field of Classification Search
CPC .......... C02F 1/685; C02F 1/688; C02F 1/722; C02F 3/342; C02F 3/343; C02F 2101/32; C02F 2103/001; C02F 2305/06; C12N 11/02; C12N 11/04; C12N 11/10; C12N 11/12
USPC ....... 210/170.03, 198.1, 209, 601, 606, 610, 210/611, 615, 631, 632; 435/174, 175, 435/177, 178, 17
See application file for complete search history.

(56) References Cited

U.S. PATENT DOCUMENTS

| 3,873,685 | A | * | 3/1975 | Kibbel, Jr. | ............. | A61K 8/046 |
| | | | | | | 424/405 |
| 3,989,596 | A | * | 11/1976 | Long | ............................. | 435/174 |
| 4,826,661 | A | | 5/1989 | Copeland et al. | | |

(Continued)

FOREIGN PATENT DOCUMENTS

WO    WO-2011/149651 A1    12/2011

OTHER PUBLICATIONS

Megazyme International Ireland, bacillus licheniformis, Material Safety Data Sheet, 6 pages.*

(Continued)

*Primary Examiner* — Patrick Orme
(74) *Attorney, Agent, or Firm* — Marshall, Gerstein & Borun LLP

(57) ABSTRACT

A device for the treatment of waste material in a waste water collection system includes an inner core and an outer portion partially surrounding the inner core such that at least one surface of the inner core is exposed. The inner core has a greater water solubility than the outer portion. In another aspect, a device for the treatment of waste material in a waste water collection system includes an outer portion defining a hollow core portion, the hollow core portion defining an interior and having at least one end plug sealing said interior against ambient atmosphere, the outer portion partially surrounding the hollow core portion such that only the end plug is exposed. The end plug has a greater water solubility than the outer portion. Methods of treating waste material in a waste water collection system are also provided.

28 Claims, 3 Drawing Sheets

(56) References Cited

U.S. PATENT DOCUMENTS

| | | | |
|---|---|---|---|
| 5,770,079 A | | 6/1998 | Haase |
| 5,807,724 A | | 9/1998 | Resnick |
| 5,925,252 A | * | 7/1999 | Cline .................... 210/606 |
| 6,039,875 A | | 3/2000 | Christiansen et al. |
| 6,150,316 A | | 11/2000 | Scepanski |
| 6,156,715 A | | 12/2000 | Lentsch et al. |
| 6,248,234 B1 | | 6/2001 | Cline |
| 6,248,324 B1 | | 6/2001 | Fischetti et al. |
| 6,325,934 B1 | | 12/2001 | Tobey, Jr. et al. |
| 6,428,701 B1 | | 8/2002 | Mullennix et al. |
| 7,148,033 B2 | * | 12/2006 | Brenner et al. ............. 435/34 |
| 7,658,851 B2 | | 2/2010 | Nelson et al. |
| 7,828,975 B2 | | 11/2010 | Oya |
| 2004/0040903 A1 | | 3/2004 | Burke et al. |
| 2005/0040116 A1 | | 2/2005 | Purdy et al. |
| 2006/0011538 A1 | | 1/2006 | Mussari et al. |
| 2006/0122086 A1 | | 6/2006 | Albu et al. |
| 2006/0272205 A1 | * | 12/2006 | Bissonnette et al. .......... 47/57.6 |
| 2008/0017574 A1 | | 1/2008 | Lenger et al. |
| 2008/0169239 A1 | | 7/2008 | Sparks et al. |
| 2009/0054287 A1 | | 2/2009 | Smith et al. |
| 2009/0148573 A1 | * | 6/2009 | Kitamura et al. ............ 426/323 |
| 2009/0283466 A1 | * | 11/2009 | Martin et al. ................ 210/209 |
| 2012/0255901 A1 | | 10/2012 | Thorgersen et al. |
| 2012/0298577 A1 | | 11/2012 | Thorgersen et al. |

OTHER PUBLICATIONS

Chemtura Corporation, bacillus subtilis Material Safety Data Sheet, 2007, 7 pages.*

"Innovative Formulations Inc., Catalog," Microxyme Bio-Remediation Technologies (2009). Retrieved from the Internet on Mar. 8, 2011: URL:http://www.innovationonline.com/pdfs/catalog/microxyme-brochure.pdf.

"Material Safety Data Sheet," Grotek Manufacturinc. Inc. (2001). Retrieved from the Internet on Mar. 9, 2011: URL:http://www.hydrofarm.com/downloads/fc/GT%20oxycal_31687.pdf.

"Multi-Strain Spore Based Formulation: High Impact Grease Digester of Lift Stations, Collection Systems, Municipalities or Industries," MicroClear 1XF-HC (2003). Retrieved from the Internet on Mar. 16, 2011: URL:http://www.environmentalleverage.com/microclear1xfhc.htm.

"OxyCal—Oxygen Generating Compound," Rex-Bac-T © Technologies (2009). Retrieved from the Internet on Mar. 16, 2011: URL:http://www.rex-bac-t.com/p-45-oxycal-oxygen-generating-compound.aspx.

"Septic Tank Treatment—Economy Paks (EP-303)," Rex-Bac-T © Technologies (2009). Retrieved from the Internet on Mar. 16, 2011: URL:http://rexbact.net/p-18-septic-tank-treatment-economy-paks-ep-303.aspx.

"Solid Slow-Dissolving Bacterial Block," Pro Chem—Bio Block (2011). Retrieved from the Internet on Mar. 7, 2011: URL:http://www.procheminc.com/product_details.asp?ID=93&cat=2.

"Solid Slow-Dissolving Bacterial Block: Product Information Sheet," Pro Chem—Bio Block #3423 (2011). Retrieved from the Internet on Mar. 7, 2011: URL:http://www.procheminc.com/prod-docs/BIO_BLOCK[2].pdf.

International Search Report and Written Opinion for Application No. PCT/US2013/038170, dated Nov. 7, 2013.

Roheim, "Low Cost Automated on Site System for Growing and Dispensing Vegetative Bacteria," (2005).

The EnduroSolv Solution, "Twelve Principles of Green Chemistry," (1998).

* cited by examiner

WATER-DISSOLVABLE DEVICE FOR TREATMENT OF WASTE MATERIAL

FIELD OF INVENTION

The invention is generally related to a water-dissolvable device for the treatment of waste material in a waste water collection system.

BACKGROUND OF THE INVENTION

Sewage is the spent water carrying body wastes, washing water, food preparation wastes, laundry wastes, and other waste products. Sewage from individual residential and commercial outflows is typically collected and processed at a central treatment plant. At the central treatment plant, sewage is treated to various stages to allow the resulting product to pass back into the ecological system. Certain types of sewage outflows have high contents of organic matter such as greases. Such organic matter can clog sewage collection systems prior to the sewage reaching the central sewage treatment plant, thereby substantially disrupting the treatment process, particularly at the lift/pumping stations frequently located along the sewage transport lines which transport the sewage to a higher elevation. Because of their utilization of pumping to transport sewage, lift stations serve as a collection point for grease and other organic matter that is not decomposed within the water flow. It is typical to regularly clean out lift stations (and other junction points in the system where floating grease and other organic matter collects) by pumping the grease and organic matter to a secondary reservoir such as a vacuum truck.

Bacterial augmentation has been implemented to maximize the effectiveness of organic decomposition in order to mitigate the problem of frequent removal of the floating grease and organic matter from lift stations (and other junction points). For example, bacteria with high capacity for increasing the decomposition of grease and other organic matter have been charged into sewage systems. Such bacteria reduce the amount of grease by converting it to lower molecular weight compounds which do not readily accumulate/agglomerate within the sewage collection system. These bacteria operate almost exclusively in the water phase and their cultures grow in the grease and water interface, on the sides and on the bottom of the tank or trap in which they are placed.

However, bacteria which compete with the added supplemental bacteria constantly enter the system with the continuous inflows of fresh sewage. Consequently, the supplemental bacteria must be replenished frequently, often daily. Liquid compositions containing bacteria can be pumped into lift stations systems but the dispensing equipment takes up needed space and as stated previously the bacteria must be added frequently.

U.S. Pat. No. 5,925,252 describes a bioremediation device for biological degradation of a waste material in a collection system. The disclosed bioremediation device comprises a bioactive element having at least one active ingredient present in a variable concentration, said variable concentration being greatest substantially at the outside of said bioactive element and being least within the bioactive element, so that the bioremediation effect of the element is greatest when the waste material is first exposed to the outside of the bioactive element and lessens as the bioactive element dissolves in the waste materials. The '252 patent remediation device thereby purports to accomplish both an initial stronger effect to achieve reduction in the grease and other organic materials in the collection system and then a diminishing effect to sustain maintenance of the remediation effect in the collection system.

SUMMARY OF THE INVENTION

In one embodiment, the invention provides a device for the treatment of waste material in a waste water collection system, the device comprising an inner core comprising a first water-soluble material, the inner core further comprising an inner agent selected from the group consisting of oxygen generating materials, enzymes, bacteria, nutrients, flocculants, and mixtures thereof, and an outer portion comprising an outer agent distributed in a binder matrix of a second water-soluble material, the outer portion partially surrounding the inner core such that at least one surface of the inner core is exposed to ambient atmosphere, the outer agent being selected from the group consisting of oxygen generating materials, enzymes, bacteria, nutrients, flocculants, and mixtures thereof, the outer agent being the same or different from the inner agent, and the first water-soluble material of the inner core having a greater water solubility than the second water-soluble material of the outer portion.

In a related embodiment, the invention provides a method of treating waste material in a waste water collection system, the method comprising contacting waste material in a waste water collection system with a device comprising an inner core comprising a first water-soluble material, the inner core further comprising an inner agent selected from the group consisting of oxygen generating materials, enzymes, bacteria, nutrients, flocculants, and mixtures thereof, and an outer portion comprising an outer agent distributed in a binder matrix of a second water-soluble material, the outer portion partially surrounding the inner core such that at least one surface of the inner core is exposed to ambient atmosphere, the outer agent being selected from the group consisting of oxygen generating materials, enzymes, bacteria, nutrients, flocculants, and mixtures thereof, the outer agent being the same or different from the inner agent, and the first water-soluble material of the inner core having a greater water solubility than the second water-soluble material of the outer portion, thereby causing the inner agent to be released into the waste material before the outer agent.

In yet a further related embodiment, the invention provides a device for the treatment of waste material in a waste water collection system, the device comprising an outer portion defining a hollow core portion, the hollow core portion defining an interior and having at least one end plug sealing said interior against ambient atmosphere, the outer portion partially surrounding the hollow core portion such that only the end plug is exposed to the ambient atmosphere, the outer portion comprising an outer agent distributed in a binder matrix of a water-soluble material, the outer agent being selected from the group consisting of oxygen generating materials, enzymes, bacteria, nutrients, flocculants, and mixtures thereof, the hollow core portion containing in the interior an inner agent selected from the group consisting of oxygen generating materials, enzymes, bacteria, nutrients, flocculants, and mixtures thereof, the inner agent being the same or different from the outer agent, and, the end plug comprising a water-soluble material having a greater water solubility than the binder matrix of the outer portion.

DETAILED DESCRIPTION

Figure 1:
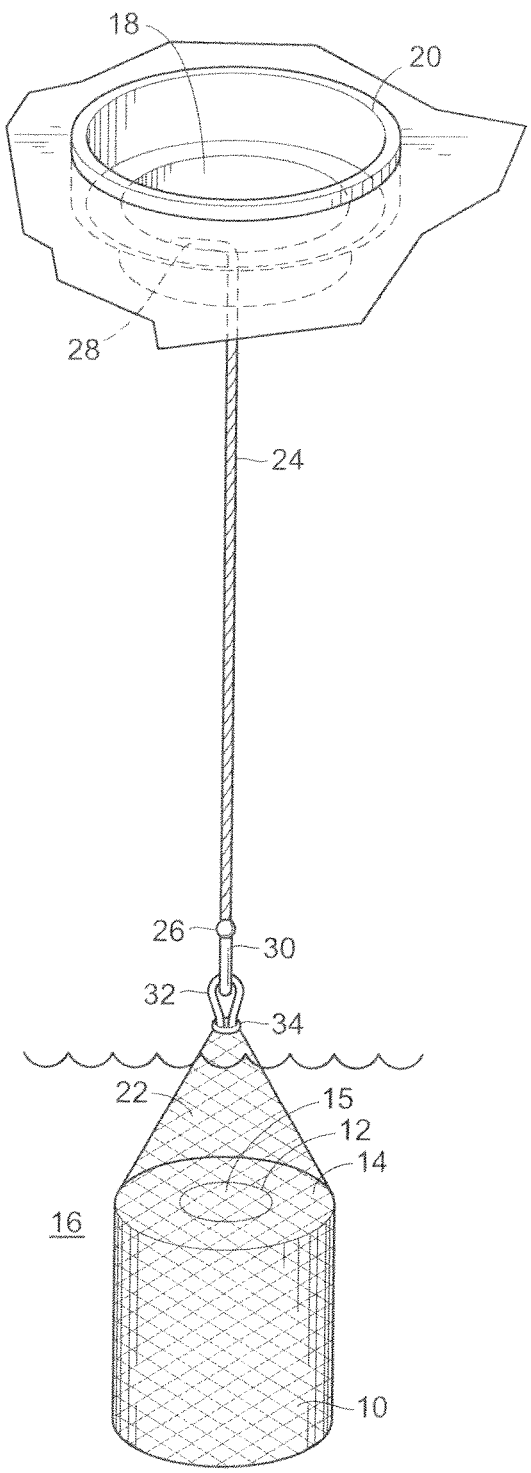
FIG. 1 illustrates application of device for the treatment of waste material in its intended aqueous waste water collection system environment.

The invention advantageously provides a device for the treatment of waste material in a waste water collection system, the device comprising an inner core comprising a first water-soluble material, the inner core further comprising an inner agent selected from the group consisting of oxygen generating materials, enzymes, bacteria, nutrients, flocculants, and mixtures thereof, and an outer portion comprising an outer agent distributed in a binder matrix of a second water-soluble material, the outer portion partially surrounding the inner core such that at least one surface of the inner core is exposed to ambient atmosphere, the outer agent being selected from the group consisting of oxygen generating materials, enzymes, bacteria, nutrients, flocculants, and mixtures thereof, the outer agent being the same or different from the inner agent, and the first water-soluble material of the inner core having a greater water solubility than the second water-soluble material of the outer portion.

As a result of the first water-soluble material of the inner core having a greater water solubility than the second water-soluble material of the outer portion and the (at least one) surface of the inner core being exposed to ambient atmosphere, when the device is contacted with a waste material (which is typically mostly water), the inner core dissolves more rapidly than the outer core portion such that the inner agent of the inner core is released into the aqueous waste water collection system environment before release of the outer agent from the outer core portion commences. Consequently, the (previously released) contents of the inner core can advantageously enhance, improve, and/or assist the performance of the contents of the outer portion upon (subsequent) release of the contents of the outer portion into the use environment.

In one example, the inner core can release a high concentration of the inner agent quickly upon introduction of the device into the waste material in order to achieve (relatively) immediate restoration of a waste water collection system, followed by (relatively) sustained release of a lower concentration of the outer agent from the outer portion to thereafter maintain the waste water collection system. In this example, the inner agent and the outer agent can be from the same class of agents, i.e., for example, both can comprise bacteria or flocculants, etc.

In a further example, the inner agent released by the inner core can promote the efficacy of the outer agent released by the outer core. In this example, the inner agent and the outer agent can be from different classes of agents. For example, the inner core can initially release nutrients which can then facilitate more rapid and successful growth of bacteria subsequently released from the outer core portion. In another example, the inner core can release bacteria capable of degrading higher molecular weight organic matter into lower molecular weight organic matter and the outer portion can release bacteria capable of degrading the lower molecular weight organic matter produced by the bacteria of the inner core. In a further example, the inner core can release a flocculant capable of removing most contaminants from waste water by facilitating sludge formation and the outer portion can release bacteria capable of degrading the formed sludge. In an additional example, the inner core can release enzymes capable of accelerating breakdown of various types of organic matter and the outer portion can release bacteria capable of degrading the residual organic matter. Of course, combinations of oxygen generating materials, enzymes, bacteria, nutrients, and flocculants can be included in either the inner core or the outer portion.

In yet another example, the inventors found that oxygen generating materials released into aqueous waste material can produce hydrogen peroxide in situ, which can detrimentally interfere with the desired biological activity of any bacteria and/or enzymes subsequently released from the device. Because the inner core is dissolved faster than the outer portion, however, the oxygen generating materials can be released from the device such that they are not in the vicinity of any bacteria/enzymes released from the outer portion if/when any hydrogen peroxide is generated; this is particularly the case when the oxygen generating material is in granular or powder form and released from a hollow interior of the device. Thus, the oxygen generating material can effectively produce oxygen for bacteria subsequently released from the outer portion without interfering with the biological activity thereof.

In use, the device of the invention is typically submerged in the waste material of grease traps, lift stations and the like. As the device dissolves, the released contents facilitate degradation and digestion of organic matter present in the waste material. For example, any released bacteria and enzymes digest organic matter in waste water (such as grease, feed, fat, and sludge), thereby dissipating strong odors and rendering the waste material more fluid. Any released flocculants facilitate sludge formation and thereby make subsequent digesting of the organic matter in the waste water by bacteria and/or enzymes more facile. Any released nutrients and oxygen generating materials promote growth of bacteria capable of digesting the organic matter. Release of the device contents in the waste material therefore enhances flow of waste material throughout the waste collection system and increases the amount of waste material that can be processed therein.

FIG. 1 illustrates application of device 10 for the treatment of waste material in its intended aqueous waste water collection system environment. Specifically, device 10 comprises an inner core 12 and an outer portion 14 (only) partially surrounding the inner core 12. Because the outer portion 14 only partially surrounds the inner core 12, at least one surface 15 of the inner core 12 is exposed to its ambient environment. As illustrated in FIG. 1, device 10 is suspended in waste material 16 from an opening 18 of a waste collection system 20 such as a drain field, grease trap, lift station, manhole inlet, and other access points to gravity lines/sewage mains. While the devices 10 can be used to treat junction points in the system where floating grease and other organic matter collects, it should be noted that the devices 10 can also be used at points upstream of such junction points (where build-up of organic matter is not present). In use, the device 10 is at least partially, and preferably completely, immersed in the waste material 16.

The device 10 is typically enclosed within a netting 22 which allows the ingredients of the inner core 12 and the outer portion 14 to dissolve and pass through the netting 22 and directly into the waste material 16. The device 10 is typically suspended from the top of the opening 18 of waste collection system 20 using a line 24 having a first end 26 and a second end 28. The line 24 is preferably made of a material that will retain and suspend the device 10 in the waste material 16 of the waste collection system 20 until the device 10 is removed therefrom by a user (usually when the device 10 is spent, i.e., has substantially dissolved in the waste material 16).

The first end 26 of the line 24 can include a clip 30 or the like for removable attachment to a loop 32 formed from the netting 22. Alternatively, line 24 can be tied directly to the loop 32. In a preferred embodiment, the netting 22 should be able to be shaped in order to form the loop 32. A ring 34 or similar device for gathering a portion of the netting above the device 10 can facilitate attachment of the clip 30 or the line 24 to the loop 32. The netting 22 is preferably formed to permit substantially unimpeded exposure of the device 10 to the waste material 16 (including water) within the collection system 20. The ring 34 may be constructed using any suitable material which is not dissolvable in water such as plastics and metals.

The second end 28 of the line 24 is detachably secured at the top of the opening 18. To position the device 10 according to the invention within the waste collection system 20, the device 10 within the netting 22 is lowered through opening 18 at the top of the collection system 20 into the waste material 16 while being coupled to the line 24. A cover (not shown) can close access to the opening 18 to the waste collection system 20 when access is not needed.

Preferably, the density of the device 10 is sufficient to keep the device 10 submerged in the waste material 16. As the device 10 dissolves, however, the device 10 may eventually float to the water surface as a result of reduced density resulting in part from dissolution of and/or ingredient release from the inner core 12 and the natural buoyancy of the netting 22, thereby providing an indication that the device 10 has almost substantially dissolved and approached the end of its useful life. Thus, the present embodiment provides an easy way of determining the device 10 change-out time. To remove the spent device 10 once it is substantially dissolved, the line 24 is pulled back through the opening 18 in the collection system 20, thereby retrieving netting 22 and any residual remains of the device 10. The spent device 10 may be replenished by coupling a fresh device 10 to the line 24 (e.g., as described above) and lowering fresh device 10 through the opening 18 such that fresh device 10 is in contact with the waste material 16.

The device 10 may be a cylinder, for example, between about 9 and about 16 inches in height and having a diameter of between about 2 and about 5 inches. Although illustrated as having a cylindrical shape, the device 10 of the present invention is not limited to any particular shape provided that it includes an inner core 12 and an outer portion 14 only partially surrounding the inner core 12, as described herein. Suitable alternative shapes for the device include but are not limited to spherical and rectangular. The device 10 can also be provided in the shape of a puck, disk, pellet, or any other suitable shape. When formulated in a small shape, e.g., a puck, disk, or other small shape, a number of devices 10 can be dropped through the opening 18 into the waste material 16 for dissolving therein, without need for utilization of line 24 or netting 22. Such smaller shapes are particularly useful for treating waste material in smaller containment areas such as grease traps and the like.

Preferably, the device 10 is configured to dissolve in approximately 90 days within systems having flow under 50,000 gallons per day. For systems having a flow of up to 100,000 gallons per day, the device 10 preferably dissolves in approximately 60 days. For systems having a flow of up to 150,000 gallons per day, the device 10 preferably dissolves in approximately 30 days. The number of days that the device 10 lasts is not particularly significant, but rather only represents approximate periods depending on device 10 compositions, waste material 16 composition, temperature, flow contact, and other similar factors.

Outer Portion

The outer portion 14 comprises an outer agent selected from the group consisting of oxygen generating materials, enzymes, bacteria, nutrients, flocculants, and mixtures thereof, bacteria and/or enzymes which is distributed in a binder matrix of a water-soluble material. As the outer portion 14 is dissolved in the waste material 16, the outer portion releases the outer agent into the waste material 16, thereby enhancing decomposition of waste materials such as floating grease and organic matter in the waste collection system 20, flow of such waste materials, and the amount of waste material that can be processed. Suitable compositions for the binder matrix of the outer portion 14 and suitable bacteria for same are disclosed in U.S. Pat. Nos. 6,248,324 and 5,925,252, which are hereby incorporated herein by reference. Suitable matrix materials and bacteria are also described below.

The water-soluble binder matrix material of the outer portion 14 can comprise about 10% to about 50%, about 30% to about 40%, and/or about 33% to about 38% by weight of a blend of biodegradable surfactants. The surfactants and their concentration in the outer portion 14 are selected to easily structurally degrade by the water flow across their surface and to create critical micelle concentrations with the grease in the waste water containment area. The surfactants generally comprise hydrophilic and/or hydrophobic portions that easily form emulsions with the sewage material and/or grease present in the waste material 16 by way of micelle formation. These surfactants preferably comprise, but are not limited to, nonionic surfactants and/or anionic surfactants.

Suitable nonionic surfactants include but are not limited to: alkanolamides (e.g., ethoxylated alkanolamides, mono-ethanolamides, mono-isopropanolamides, and modified alkanolamides), polyoxyethylene fatty alcohol ethers, polyoxyethylene sorbitan fatty acid esters, alkyl polyoxyethylene sulfates, polyoxyethylene fatty acid esters, sorbitan esters, glyceryl esters, glycerol monostearate, polyethylene glycols, polyethylene glycol esters, polypropylene glycols, polypropylene glycol esters, sorbitol esters (e.g., ethoxylated sorbitol esters), aromatic ethoxylates (e.g., octyphenol aromatic ethoxylates, nonylphenol aromatic ethoxylates, dionylphenol aromatic ethoxylates, dodecylphenol aromatic ethoxylates, and tristyrylphenol ethoxylates), alcohol ethoxylates (e.g., isotridecyl alcohol ethoxylates, isodecyl alcohol ethoxylates, and oleyl alcohol ethoxylates), cetyl alcohol, cetostearyl alcohol, stearyl alcohol, aryl alkyl polyether alcohols, polyoxyethylene-polyoxypropylene copolymers, poloxamers, poloxamines, methylcelluloses, hydroxycelluloses, hydroxymethylcelluloses, hydroxyethylcelluloses, hydroxypropylcelluloses, hydroxypropylmethylcelluloses, noncrystalline cellulose, polysaccharides, starch, starch derivatives, hydroxyethylstarch, polyvinyl alcohol, polyvinylpyrrolidone, coconut monoethanolamines, triethanolamine stearate, amine oxides, dextran, glycerol, gum acacia, cholesterol, tragacanth, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, 4-(1,1,3,3-tetramethylbutyl)phenol polymer with ethylene oxide and formaldehyde, poloxamers, alkyl aryl polyether sulfonates, mixtures of sucrose stearate and sucrose distearate, p-isononylphenoxypoly(glycidol), decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside; nonanoyl-N-methylglucamide, n-nonyl-β-D-glucopyranoside, octanoyl-N-methylglucamide, n-octyl-β-D-glucopyranoside, octyl-β-D-thioglucopyranoside, PEG-cholesterol, PEG-cholesterol derivatives, PEG-vitamin A, PEG-vitamin E, and random copolymers of vinyl acetate and vinyl pyrrolidone. The hydrophilic portion of the non-ionic surfactant preferably comprises at least one and preferably multiple polar ether linkages derived from polymerization of ethylene oxide and/or propylene oxide.

Suitable anionic surfactants carry a negative charge on the hydrophilic portion, such as in the form of carboxylates, phosphates, sulfates, and/or sulfonates. Suitable anionic surfactants include but are not limited to: alkyl sulfonates, aryl sulfonates, alkyl phosphates, alkyl phosphonates, alkyl sulfates, ether sulfates, dodecylbenzene sulfonates, alpha olefin sulfonates, diphenyloxide disulfonate, alkyl naphthalene sulfonates, sulfosuccinates, sulfosuccinamates, naphthalene-formaldehyde condensates, sulfonesters, sulfoamides, fatty acid taurates, fatty acid isethionates, phosphate esters, ether carboxylates, potassium laurate, sodium lauryl sulfate, sodium dodecylsulfate, alkyl polyoxyethylene sulfates, sodium alginate, dioctyl sodium sulfosuccinate, phosphatidic acid and their salts, sodium carboxymethylcellulose, bile acids and their salts (e.g., cholic acid, deoxycholic acid, glycocholic acid, taurocholic acid, and glycodeoxycholic acid), calcium carboxymethylcellulose, carboxymethylcellulose sodium, stearic acid and its salts (e.g, calcium stearate), phosphates, sodium dodecylsulfate, dioctylsulfosuccinate, dialkylesters of sodium sulfosuccinic acid, phospholipids, and/or mixtures thereof.

The outer portion 14 binder matrix may additionally comprise about 1% to about 20% and/or about 3% to about 4% by weight of sodium thiosulfate which neutralizes the presence of chlorine ions in the waste system. The outer portion 14 may further comprise about 1% to about 20% and/or about 1% to about 2% by weight of citric acid.

The outer portion 14 binder matrix also typically includes sodium sulfate, sodium sulfite, sodium nitrate, sodium nitrite, and/or mixtures thereof. The cationic portion of the aforementioned salts may alternatively (or additionally) include calcium, potassium, or magnesium. The sulfate and/or sulfite ionic portions aid in the decomposition process through the sulfate reduction cycle, which reduces sulfides such as hydrogen sulfide ($H_2S$) and ferrous sulfide (FeS) which can create corrosion and odor problems in the waste system. The nitrate and/or nitrite ionic portions aid in the decomposition process through the nitrification cycle.

The outer portion 14 binder matrix further includes an outer agent selected from the group consisting of oxygen generating materials, enzymes, bacteria, nutrients, flocculants, and mixtures thereof. Frequently, the outer portion comprises bacteria and/or enzymes having a capacity for decomposing and/or degrading organic matter distributed therein. When present in the outer portion 14, a blend of bacteria of at least about 5 billion colony forming units (CFU's) per gram material or greater (e.g., at least 10 billion CFU's per gram, at least 20 billion CFU's per gram, or even more) typically are included in the outer portion 14 in an amount of about 10% to about 50%, about 30% to about 40%, and/or about 32% to about 38% by weight (based on the weight of the outer portion). Suitable genera of bacteria (defined herein as being inclusive of biovars thereof) for use in device 10 include are described below.

The dissolvability of the outer portion 14 may be increased or decreased by increasing or decreasing the surfactant concentration in the outer portion or by varying the functional group of the surfactant. For example, a class of surfactants commonly known as alkanolamine soaps are reacted by combining an amine and a fatty acid. A preferred embodiment of the present invention utilizes biodegradable alkanolamine surfactants having differing combinations of the amine and the fatty acid in order to adjust the dissolvability in accordance with the water flow of a specific waste collection system 20. For example, reaction of a coconut oil with monoethanolamine yields a relatively softer carrier that dissolves relatively fast in lower flow situations, whereas substitution of stearic acid for the coconut oil allows the carrier to be relatively slower in dissolving properties and more preferable for higher flow situations. Further, the surface texture of outer portion 14 can be solid/smooth, pitted, porous, or otherwise modified as known to those skilled in the art, in order to affect the dissolution rate thereof.

Inner Core

The inner core 12 is typically substantially surrounded by the outer portion 14, but at least one surface 15 of the inner core 12 is exposed to the ambient environment (in FIG. 1, the ambient environment is waste material 16). According to the invention, the water-soluble material of the inner core 12 has a greater water solubility than the water-soluble material outer portion 14. Because the water-soluble material of the inner core 12 has a greater water solubility than the water-soluble material of the outer portion 14 and at least one surface 15 of the inner core 12 is exposed to the ambient atmosphere of aqueous waste material 16, when the device 10 is submerged in the waste material 16, the contents/ingredients of the inner core 12 are released into the (predominantly aqueous) waste material 16 of the waste collection system 20 before release of the contents/ingredients of the outer core portion commences. Consequently, the (previously released) contents of the inner core 12 can advantageously improve the performance of the contents of the outer portion 14 upon release of the contents of the outer portion 14 into the use environment 16.

Figure 2:
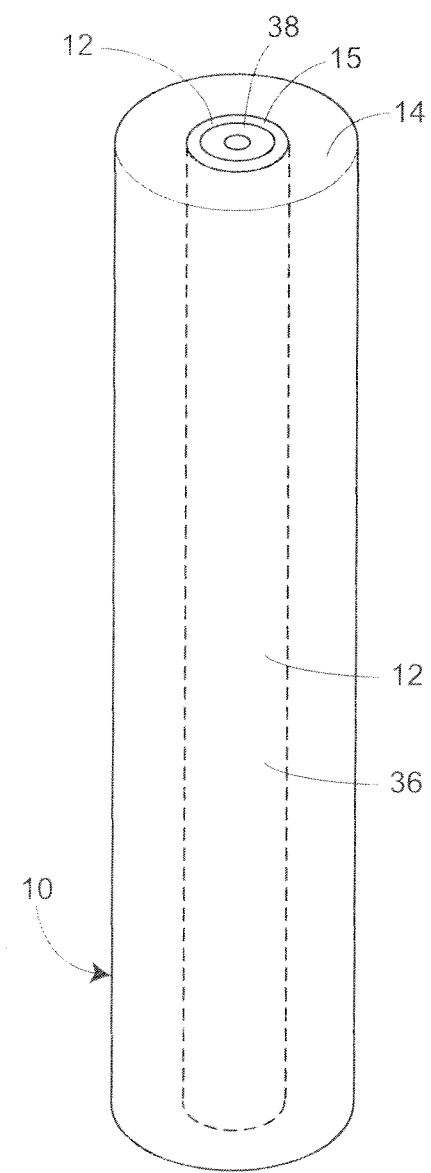
FIG. 2 illustrates one embodiment of a device in accordance with the invention, the device having an inner core comprising a hollow interior and one or more end plugs sealing said hollow interior.

As illustrated in FIG. 2, in one aspect, the inner core 12 of the device 10 comprises a hollow interior 36 and one or more end plugs 38 sealing said hollow interior 12. The one or more end plugs 38 of the inner core 12 are exposed to the ambient waste material environment 16 (when submerged) and thus provide the at least one exposed surface 15 of the device 10. The surface texture of the end plug(s) 38 of the inner core 12 can be solid/smooth, pitted, porous, or otherwise as known to those skilled in the art, in order to adjust the dissolution rate of the end plug(s) 38 of the inner core 12.

Figure 3:
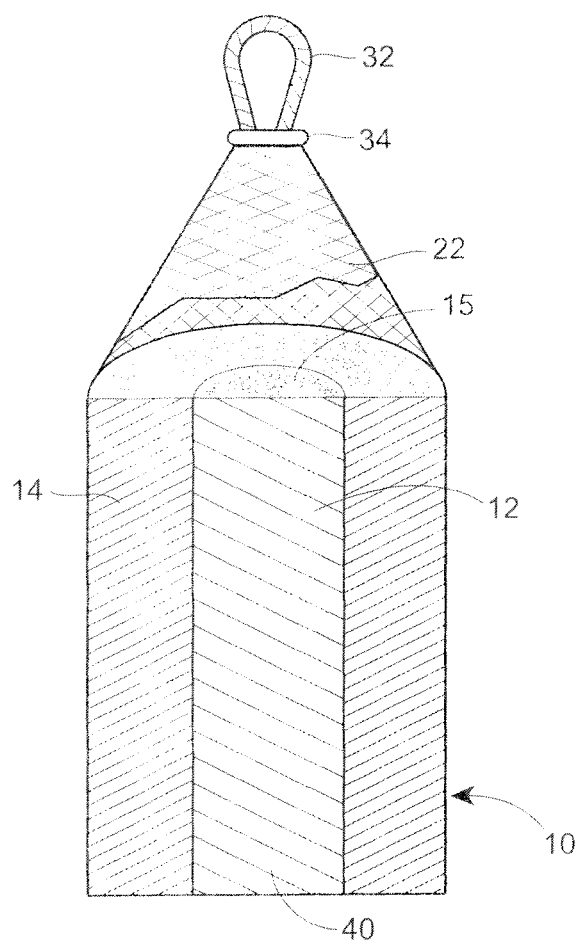
FIG. 3 illustrates a second embodiment of a device in accordance with the invention, the device having an inner core comprising a binder matrix material.

As illustrated in FIG. 3, in another aspect, the inner core 12 of the device 10 comprises a binder matrix material 40 partially contained within and/or surrounded by the outer portion 14. The binder matrix material 40 can substantially and continuously fill the outer portion provided that at least one surface 15 of the inner core 12 is exposed to the ambient waste material environment 16 (when submerged). Because the binder matrix material 40 dissolves faster than the binder matrix material of the outer core portion 14, it is necessarily different from the binder matrix material of the outer core portion 14. Although the end plugs 38 are not shown in conjunction with the device including the inner core 12 comprising the binder matrix material 40, a combination of end plugs 38 and binder matrix material 40 can also be used in the inner core 12 in accordance with the invention provided that the water-soluble materials of the end plugs 38 and the binder matrix material 40 have a greater water solubility than the water-soluble material of the outer portion 14.

In both of the aspects shown in FIGS. 2 and 3, the water-soluble material of the inner core 12 has a greater water solubility than the water-soluble material of the outer portion 14. Preferably, the respective materials of the end plug(s) 38 and/or the binder matrix 40 have a water solubility value of greater than or equal to 1 mg/mL, preferably greater than or equal to 5 mg/mL, and even more preferably greater than or equal to 10 mg/ml. Both the end plug(s) 38 and the matrix 40 can comprise a water-soluble material selected from the group consisting of methylhydroxycelluloses, methylcelluloses, ethylcelluloses, hydroxyethylcelluloses, carboxymethylcelluloses, methylhydroxypropylcelluloses, hydrolyzed corn starches, hydrolyzed potato starches, gum arabic, guar gum, locust bean gum, carrageenans, karaya gums, ghatti gums, tragacanth agars, tamarind gums, xanthan gums, microcrystalline celluloses, sodium alginates, konjac glucomannans, pullulans, pectins, arabinogalactans, and mixtures thereof.

Further in both of the aspects shown in FIGS. 2 and 3, the inner core 12 can be colored using a different color (e.g., pigment or dye) than that of the outer portion 14. Using different colors for the end plug(s) 38 and/or the binder matrix 40 of the inner core relative to that of the outer portion 14 can facilitate a user's ability to detect whether the inner core 12 has been expended. Moreover, using different colors for the end plug(s) 38 and/or the binder matrix 40 relative to that of the outer portion 14 can also create a pleasing aesthetic effect.

When the device 10 comprises an inner core 12 having a hollow interior 36 and one or more end plugs 38 sealing, said hollow interior 36, the inner agent may be provided in granular form. The granular nature of the inner agent of the inner core 12 can facilitate the release thereof from the inner core 12 such that the inner agent is not in the immediate vicinity of the outer portion 14 upon the subsequent dissolution and release of the outer agent from the outer portion 14. This can be particularly beneficial when an oxygen generating material is included in the inner core 12, as production of hydrogen peroxide in the immediate vicinity of the outer core portion 14 can detrimentally interfere with the desired biological activity of any bacteria and/or enzymes contained within and released from the outer portion 14 of the device 10.

Such an effect can also be observed, even if somewhat attenuated, when the inner core 12 comprises a binder matrix material 40 and the inner agent is distributed therein. Thus, according to both aspects of the inner core 12 according to the invention, because the inner core 12 is dissolved faster than the outer portion 14, the inner agent can be released from the device such that the inner agent is not in the immediate vicinity of the outer portion 14 upon the subsequent dissolution and release of the outer agent from the outer portion 14, particularly when the oxygen generating materials is in granular form and released from a hollow interior 36 of the device 10.

Inner and Outer Agents

The inner core 12 and the outer portion 14 comprise at least one of oxygen generating materials, enzymes, bacteria, nutrients, and flocculants, as contents/ingredients which are released into the (predominantly aqueous) waste material 16 of the waste collection system 20.

Often, aerobic degradation of waste materials by bacteria is limited by oxygen availability in the waste material 16. Thus, supplemental release of oxygen can speed digestion of solid wastes in the waste material 16. Specifically, the oxygen releasing materials are capable of enhancing and promoting the bacterial population dynamics by supplying the right oxygen requirements that bacteria need for their respiration processes. Suitable oxygen generating materials for the inner core and the outer portion may be selected from the group consisting of peroxides, percarboxylics, percarbonates, and mixtures thereof. Most preferably, the oxygen generating agent, if present, is contained in the inner core 12. Suitable oxygen generating materials are disclosed in U.S. Patent Publication No. 2006/0272205, which is hereby incorporated by reference. One exemplary commercially available oxygen generating material available in powder form is sold under the trade name OXY CAL™ (Rex-Bac-T Technologies, Ga.).

When present in the inner core 12 and/or the outer portion 14, a blend of enzymes may be used. Suitable enzymes are capable of accelerating breakdown of various types of organic matter frequently found in waste material. Typically, the enzymes are selected from lipases, amylases, proteases, xylanases, and cellulases (e.g., cellulase esterase). Suitable enzyme containing materials may contain lipases in an amount between 100 and 10,000 and/or 200-800 units per gram material, amylases in an amount between 10,000 and 200,000 and/or 20,000 and 100,000 units per gram material, proteases in an amount between 3000 and 100,000 and/or 15,000 and 60,000 units per gram material, and/or cellulases in an amount between 10 and 2000 and/or 50 and 500 units per gram material.

Suitable bacteria for the inner core 12 and outer portion 14 include but are not limited to gram positive bacteria such as *Bacillus licheniformis, Bacillus sphaericus, Bacillus subtilis, Bacillus pumilus, Bacillus amyloliquefaciens, Bacillus megaterium, Bacillus cereus, Bacillus thuringiensis, Bacillus polymyxa, Arthrobacter petroleophagus, Arthrobacter parraffineus, Rhodoccus erythropolis*, other strains of *Rhodocuccus*, and gram negative bacteria such as *Rhodobacter sphaeroides, Rhodobacter capsulatus, Pseudomonas putida, Pseudomonas aeruginosa, Pseudomononas stutzeri, Pseudomonas fluorescens, Achromobacter* strains, *Escherichia hermanii*, and/or mixtures thereof. Preferably, if included, bacteria in the inner core comprises rapid growth gram negative bacteria such as the gram negative bacteria identified above, which can greatly facilitate degradation by 'jump-starting' treatment of the waste material 16. When present, a blend of bacteria of at least about 5 billion colony forming units (CFU's) per gram material or greater (e.g., at least about 10 billion CFU's per gram, at least about 20 billion CFU's per gram or even more) can be included in the inner core 12 and/or outer portion 14.

Nutrients can be included in the inner core 12 and/or the outer portion 14 to promote rapid and healthy growth of the bacteria (whether released initially from the inner core 12 or subsequently from outer core portion 14) in the waste material 16. Suitable nutrients include but are not limited to (trace) minerals, amino acids and vitamins. Suitable trace minerals include but are not limited to calcium, iron, magnesium, manganese, cobalt, copper, phosphorus, and zinc. Suitable amino acids include but are not limited to lysine, glycine, etc. Suitable vitamins include but are not limited to niacin, folic acid, ascorbic acid, vitamin A, vitamin B, vitamin D, vitamin E, and vitamin K. One exemplary commercially available oxygen generating material available in powder form is sold under the trade name MICRO-CLEAR M100™ (Environmental Leverage Inc., Ill.).

Flocculants can be included in the inner core 12 and/or the outer portion 14 to cause the solid organic and inorganic matter in the waste material 16 to flocculate and thereby facilitate sludge formation. Suitable flocculants (for both of the aforementioned inner core 12 aspects) include but are not limited to salts of multivalent metals, nonionic polymers, anionic polymers, and cationic polymers. Representative flocculants include ferric chloride, ferric sulfate, aluminum chloride, aluminum sulfate, polyacrylamide, poly(ethylene oxide), acidic compounds such as sulfuric acid, nitric acid and hydrochloric acid, dimethyl amine, epichlorohydrin, polysaccharides, mainly starch and its constituents, different types of gums, alginic acid, cellulose and its derivatives, dextran, amine homopolymers and amine copolymers containing diallyl dimethyl ammonium chloride, etc. In anionic polymer flocculants, two types of polymers are typically used: one type of polymers contain carboxyl functional groups, for example, such as poly(acrylic acid) and its derivatives; the other type of polymers contain sulfonic acid groups, for example, such as poly(styrene sulfonic acid) (PSSA). The cationic groups of the cationic polymer flocculants typically are derived by introducing quaternary ammonium groups onto the polymer backbone, although polymers containing sulfonium and phosphonium groups can be used. Cationic polymer flocculants can also be prepared by a reaction of a polysaccharide with various reagents possessing positively charged groups such as amino, imino, ammonium, sulfonium or phosphonium groups. Cationized polysaccharides are effective flocculants over a wide pH range, are non-toxic and exhibit good biodegradability. Specific examplary powdered flocculants include but are not limited to cationic polyacrylamides sold under the SUPERFLOC® trade name such as SUPER-FLOC® C-491 HMW, SUPERFLOC® C-492 HMW, SUPERFLOC® C-493 HMW, SUPERFLOC® C-494 HMW, SUPERFLOC® C-495 HMW, SUPERFLOC® C-496 HMW, SUPERFLOC® C-497 HMW, and SUPER-FLOC® C-498 HMW (Cytec Industries Inc., Conn.).

Representative Devices

Representative devices 10 can include outer portions 14 and inner cores 12 containing blends of bacteria. In one example, the outer portion 14 can comprise a blend of *Bacillus licheniformis, Bacillus sphaericus, Bacillus subtilis, Bacillus pumilus, Bacillus megaterium*, and *Bacillus polymyxa*, and the inner core can comprise a blend of *Bacillus licheniformis, Bacillus sphaericus, Bacillus subtilis, Bacillus pumilus, Bacillus megaterium*, and *Bacillus polymyxa*, and a blend of *Pseudomonas fluorescens, Pseudomonas putida, Rhodobacter sphaeroides*, and *Rhodobacter capsulatus*. In a further example, the outer portion 14 can comprise a blend of *Bacillus licheniformis, Bacillus sphaericus, Bacillus subtilis, Bacillus pumilus, Bacillus megaterium*, and *Bacillus polymyxa*, and the inner core can comprise a blend of *Pseudomonas fluorescens, Pseudomonas putida, Rhodobacter sphaeroides*, and *Rhodobacter capsulatus*. In an additional example, the outer portion 14 can comprise a blend of *Bacillus licheniformis, Bacillus sphaericus, Bacillus subtilis, Bacillus pumilus, Bacillus megaterium*, and *Bacillus polymyxa*, and the inner core 12 can comprise a granular oxygen generating material. In another example, the outer portion 14 can comprise a blend of *Bacillus licheniformis, Bacillus pumilus, Bacillus subtilis, Bacillus amyloliquefaciens*, and *Bacillus megaterium*, and the inner core can comprise a blend of *Bacillus licheniformis, Bacillus sphaericus, Bacillus subtilis, Bacillus pumilus, Bacillus megaterium*, and *Bacillus polymyxa, Pseudomonas putida, Pseudomonas fluorescens*, granular lipase, and nutrients. In yet another example, both the inner core 12 and the outer portion 14 contain cationic polyacrylamides.

The outer portion 14 of the device 10 is typically formed by an extrusion process. According to this process, a liquid mixture of the water-soluble binder material of the outer portion 14 (which contains the outer agent) is extruded and dried to form a cylindrical outer portion 14 having a hollow interior 36. The outer portion 14 has two openings in its interior 36 to ultimately provide two surfaces 15 for exposure to the ambient environment. One of these openings can then be capped, for example, with an end plug 38 or with additional water-soluble binder material of the outer portion 14 so the device 10 can then be filled with the inner agent. The inner agent can be provided substantially by itself, for example, as a granular or powdered material comprising the inner agent, or the inner agent can be distributed in a binder matrix different from the binder matrix of the outer portion 14. While the outer portion 14 can also be formed by a melt and pour process in which a traditional mold is used, such a process is generally not preferred because of its detrimental effect on the mortality and efficacy of the outer agent(s), particularly bacteria and enzymes.

The nature and amounts of the ingredients as well as the given physical dimensions of the device 10 are merely exemplary and are not meant to limit the practice of the present invention.

The invention claimed is:

1. A device for the treatment of waste material in a waste water collection system, the device comprising:
   an inner core comprising a first water-soluble material, the inner core further comprising an inner agent, and
   an outer portion comprising an outer agent distributed in a binder matrix of a second water-soluble material, the outer portion partially surrounding the inner core such that at least one surface of the inner core is exposed to ambient atmosphere, the outer agent being selected from the group consisting of oxygen generating materials, enzymes, bacteria, nutrients, flocculants, and mixtures thereof, the outer agent being the same or different from the inner agent, and the first water-soluble material of the inner core having a greater water solubility than the second water-soluble material of the outer portion, wherein the inner agent comprises gram negative bacteria.

2. The device according to claim 1, wherein the inner core comprises a hollow interior and one or more end plugs sealing said hollow interior, said end plugs comprising the first water-soluble material.

3. The device according to claim 2, wherein the end plugs comprise a material having a water solubility value of greater than or equal to 1 mg/mL.

4. The device according to claim 2, wherein the end plugs comprise a material selected from the group consisting of methylhydroxycelluloses, methylcelluloses, ethylcelluloses, hydroxyethylcelluloses, carboxymethylcelluloses, methylhydroxypropylcelluloses, hydrolyzed corn starches, hydrolyzed potato starches, gum arabic, guar gum, locust bean gum, carrageenans, karaya gums, ghatti gums, tragacanth agars, tamarind gums, xanthan gums, microcrystalline celluloses, sodium alginates, konjac glucomannans, pullulans, pectins, arabinogalactans, and mixtures thereof.

5. The device according to claim 1, wherein the inner agent is provided in granular or powder form.

6. The device according to claim 1, wherein the inner agent further comprises an oxygen generating material.

7. The device according to claim 1, wherein the inner agent is distributed in a binder matrix of the first water-soluble material.

8. The device according to claim 7, wherein the first water-soluble material is selected from the group consisting of methylhydroxycelluloses, methylcelluloses, ethylcelluloses, hydroxyethylcelluloses, carboxymethylcelluloses, methylhydroxypropylcelluloses, hydrolyzed corn starches, hydrolyzed potato starches, gum arabic, guar gum, locust bean gum, carrageenans, karaya gums, ghatti gums, tragacanth agars, tamarind gums, xanthan gums, microcrystalline celluloses, sodium alginates, konjac glucomannans, pullulans, pectins, arabinogalactans, and mixtures thereof.

9. The device according to claim 1, wherein the binder matrix of the second water-soluble material comprises a non-ionic surfactant.

10. The device according to claim 1, wherein the binder matrix of the second water-soluble material comprises an anionic surfactant.

11. The device according to claim 1, wherein the inner agent further comprises an oxygen generating material selected from the group consisting of peroxides, percarboxylics, percarbonates, and mixtures thereof.

12. The device according to claim 1, wherein the outer agent comprises one or more enzymes selected from lipases, amylases, proteases, xylanases, and cellulases.

13. The device according to claim 1, wherein the inner agent and/or the outer agent comprises a material comprising $\geq 1\times 10^{10}$ bacteria colony forming units per gram material.

14. The device according to claim 1, wherein the inner agent further comprises one or more nutrients selected from the group consisting of minerals, vitamins, and amino acids.

15. The device according to claim 1, wherein the outer agent comprises one or more flocculants selected from the group consisting of salts of multivalent metals, non-ionic polymers, anionic polymers, and cationic polymers.

16. The device according to claim 1, further comprising a netting capable of suspending the device in a waste water collection system.

17. The device according to claim 1, wherein the color of the inner core is different from the color of the outer portion.

18. The device according to claim 1, wherein the inner agent further comprises one or more of oxygen generating materials, enzymes, nutrients, flocculants, and mixtures thereof.

19. A method of treating waste material in a waste water collection system, the method comprising:
contacting waste material in a waste water collection system with a device comprising an inner core comprising a first water-soluble material, the inner core further comprising an inner agent, and an outer portion comprising an outer agent distributed in a binder matrix of a second water-soluble material, the outer portion partially surrounding the inner core such that at least one surface of the inner core is exposed to ambient atmosphere, the outer agent being selected from the group consisting of oxygen generating materials, enzymes, bacteria, nutrients, flocculants, and mixtures thereof, the outer agent being the same or different from the inner agent, and the first water-soluble material of the inner core having a greater water solubility than the second water-soluble material of the outer portion, thereby causing the inner agent to be released into the waste material before the outer agent, wherein the inner agent comprises gram negative bacteria.

20. The method according to claim 19, wherein the waste material is contacted with the device at a location selected from the group consisting of drain fields, grease traps, lift stations, and manhole inlets.

21. The method according to claim 19, wherein the inner core comprises a hollow interior and one or more end plugs sealing said hollow interior, said end plugs comprising the first water-soluble material.

22. The method according to claim 19, wherein the inner agent is distributed in a binder matrix of the first water-soluble material.

23. The method according to claim 19, wherein the color of the inner core is different from the color of the outer portion.

24. The method according to claim 19, wherein the inner agent further comprises one or more of oxygen generating materials, enzymes, nutrients, flocculants, and mixtures thereof.

25. A device for the treatment of waste material in a waste water collection system, the device comprising:
an outer portion defining a hollow core portion,
the hollow core portion defining an interior and having at least one end plug sealing said interior against ambient atmosphere,
the outer portion partially surrounding the hollow core portion such that only the end plug is exposed to the ambient atmosphere,
the outer portion comprising an outer agent distributed in a binder matrix of a water-soluble material, the outer agent being selected from the group consisting of oxygen generating materials, enzymes, bacteria, nutrients, flocculants, and mixtures thereof,
the hollow core portion containing in the interior an inner agent,
the inner agent being the same or different from the outer agent, and,
the end plug comprising a water-soluble material having a greater water solubility than the binder matrix of the outer portion, wherein the inner agent comprises gram negative bacteria.

26. The device according to claim 25, wherein the inner agent is provided in granular or powder form.

27. The device according to claim 25, wherein the color of the end plug is different from the color of the outer portion.

28. The device according to claim 25, wherein the inner agent further comprises one or more of oxygen generating materials, enzymes, nutrients, flocculants, and mixtures thereof.

* * * * *